US012653581B1

(12) United States Patent
Talwar

(10) Patent No.: US 12,653,581 B1
(45) Date of Patent: Jun. 16, 2026

(54) HYBRID PEDICLE SCREW AND SPINE ROD ASSEMBLIES

(71) Applicant: Vikram Talwar, San Ramon, CA (US)

(72) Inventor: Vikram Talwar, San Ramon, CA (US)

( * ) Notice: Subject to any disclaimer, the term of this patent is extended or adjusted under 35 U.S.C. 154(b) by 357 days.

(21) Appl. No.: 18/238,975

(22) Filed: Aug. 28, 2023

Related U.S. Application Data

(60) Provisional application No. 63/401,312, filed on Aug. 26, 2022.

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC .. A61B 17/7007–7008; A61B 17/7011; A61B 17/7013; A61B 17/7019; A61B 17/7023; A61B 17/7043; A61B 17/7049–7052
See application file for complete search history.

(56) References Cited

U.S. PATENT DOCUMENTS

| | | | |
|---|---|---|---|
| 6,558,423 | B1 | 5/2003 | Michelson |
| 6,969,390 | B2 | 11/2005 | Michelson |
| 7,608,096 | B2 | 10/2009 | Foley |
| 7,799,054 | B2 | 9/2010 | Kwak |
| 8,062,367 | B2 | 11/2011 | Kirschman |
| 8,066,749 | B2 | 11/2011 | Winslow |
| 8,882,814 | B2 | 11/2014 | Suh | |
| 9,198,696 | B1 * | 12/2015 | Bannigan | ........... A61B 17/7052 |
| 9,277,943 | B2 | 3/2016 | Holly | |
| 2002/0007183 | A1 * | 1/2002 | Lee | ..................... A61B 17/7002 606/252 |
| 2003/0060828 | A1 | 3/2003 | Michelson | |
| 2010/0030274 | A1 * | 2/2010 | Mitchell | ........... A61B 17/7005 606/264 |
| 2010/0318131 | A1 * | 12/2010 | James | ................ A61B 17/7007 606/279 |
| 2013/0172934 | A1 * | 7/2013 | Walker | ............... A61B 17/7052 606/252 |
| 2017/0079686 | A1 * | 3/2017 | Dant | .................. A61B 17/7007 |
| 2017/0311986 | A1 * | 11/2017 | McNab | .............. A61B 17/7023 |
| 2019/0117272 | A1 * | 4/2019 | Klausman | .......... A61B 17/7052 |
| 2020/0397483 | A1 * | 12/2020 | Haziza | ............... A61B 17/7023 |

* cited by examiner

*Primary Examiner* — Eduardo C Robert
*Assistant Examiner* — Michelle C Green
(74) *Attorney, Agent, or Firm* — Heisler & Associates

(57) ABSTRACT

A pedicle screw portion and a spine rod portion together form a hybrid fixation assembly of low profile form, especially in a dorsal direction. The pedicle screw portion includes a head with a threaded shaft extending therefrom. The spine rod portion includes a junction through which it is attached to the head and able to swivel about a swivel post relative to the head. In various embodiments, additional degrees of freedom, including rotation and pivoting, can be accommodated between the spine rod portion of the pedicle screw portion. A turndown screw with associated tulip head is configured to attach to a threaded bore in the head of the assembly to allow for extension dorsally and joining of the assembly with other spine rods. Various spinal stabilization and fusion procedures can be performed utilizing the assembly and future expansion is accommodated with addition of further stabilization hardware.

17 Claims, 10 Drawing Sheets

HYBRID PEDICLE SCREW AND SPINE ROD ASSEMBLIES

CROSS-REFERENCE TO RELATED APPLICATIONS

This application claims benefit under Title 35, United States Code § 119 (e) of U.S. Provisional Application No. 63/401,312 filed on Aug. 26, 2022.

FIELD OF THE INVENTION

The following invention relates to pedicle screws and spine rods for stabilizing a spine of a patient. More particularly, this invention relates to hybrid pedicle screws and spine rods where the pedicle screw and spine rod are integrated together into a common assembly, and applications for such assemblies.

BACKGROUND OF THE INVENTION

Spine rods and pedicle screws are known in the prior art to provide a fixation assembly for the spine. Such fixation assemblies are beneficial when the spine needs stabilization, such as after an injury or to correct a defect in the spine. Such fixation assemblies can be permanent or temporary.

Such fixation assemblies include two major parts: pedicle screws and at least one spine rod. The pedicle screws include a threaded shaft which threads down into a pedicle of a vertebra, or some other bone structure of the patient. A driving head of the pedicle screw typically includes some form of structure to which torque can be applied about a rotational axis of the threaded shaft (also referred to as a Z-axis), for screwing of the threaded shaft into bone. Typically, this driving head has a hexagonal recess for receiving such a torque applying tool. The prior art pedicle screws also include a tulip head and a set screw (also called a nut) which threads int threads of the tulip head and works with the driving head to capture a spine rod and secure the pedicle screw to the spine rod.

Disadvantageously, the tulip head and set screw are provided as separate structures relative to the pedicle screw, so that the pedicle screw is actually an assembly of at least three parts (the threaded shaft and driving head, the tulip head, and the set screw). Typically, while the pedicle screw is driven into bone, the tulip head is already placed upon the threaded shaft and driving head, but without firm attachment, so that the tulip head is somewhat in the way and can flop about during driving of the threaded shaft into the pedicle of a vertebra or other bone. The spine rod then needs to be placed into a saddle of the tulip head and the small separate set screw needs to be placed into the tulip head and threaded down against the spine rod to secure the overall assembly together. Not only is this a multi-step and difficult procedure, but the set screw being separate from the spine rod and tulip head can be easily dropped or misplaced before or during installation, creating complications that can be major.

Even after the fixation assembly has been placed and tightened where desired, the tulip head extends significantly away from the spine rod and up into musculature surrounding the spine, generally in a dorsal direction. With some pedicle screws, the tulip head includes extensions which can be removed after the set screw has been placed, so that the tulip head does not extend as far away from the spine rod. However, this requires an additional procedure, and still the remaining portions of the tulip head extend significantly away from the spine rod and into adjacent musculature, and can include sharp edges.

Furthermore, adjacent level degeneration is common above and below spinal fusions. Currently there is no easy way to affix a spine rod onto existing implanted hardware. One solution using devices commonly known as "domino rod connectors" (one source being under the Polaris Spinal System trademark of Zimmer Biomet Spine, Inc. of Westminster, Colorado) are bulky and difficult to affix to rods. Thus a need exists for simple low profile ways to expand spinal fusions to adjacent levels.

Accordingly, a need exists for a fixation assembly including a pedicle screw portion and a spine rod portion which can be provided either as an all-in-one single assembly, or with separate pieces which remain attached together and merely transition from floating relative to each other to being tightened relative to each other, so that risk of loss of parts of the fixation assembly can be eliminated or significantly minimized, and simplicity of installation can be improved. Furthermore, a need exists for a fixation assembly which is lower profile away from the spine rod to avoid or minimize extension of portions of the fixation assembly into adjacent musculature.

SUMMARY OF THE INVENTION

With this invention, a fixation assembly is provided which has a limited number of pieces, and which pieces are all held together, whether in a loose initial form or in a tightened final form, and which fixation assembly maintains a low profile above the spine rod, to minimize extension into adjacent musculature, dorsally. In at least three example embodiments, the pieces of the fixation assembly can have one, two or three degrees of freedom between a pedicle screw portion and a spine rod portion of the assembly.

In the first example embodiment, the fixation assembly has only one degree of freedom between the pedicle screw portion and the spine rod portion. The pedicle screw includes a threaded shaft extending along a Z-axis of rotation. The threaded shaft can have threads particularly configured to engage bone. In one embodiment the threads are self-tapping, with tapping/cutting surfaces on portions of the threads adjacent to a tip opposite a driving head of the pedicle screw.

A head of the pedicle screw, in this embodiment, is fixed to the threaded shaft, with the head typically formed from a unitary mass of material along with the threaded shaft. This head includes a torque receiving structure, such as a hexagonal recess, which is typically aligned with the Z-axis running along a long axis aligned with a centerline of rotation of the threaded shaft. The head can be enlarged radially away from this hexagonal recess or other torque receiving structure at the center of the head. Such enlarged radial structure preferably does not extend significantly (or at all) above the margins of the hexagonal recess or other torque receiving structure associated with the driving head of the pedicle screw.

The radial enlargement of the driving head of the pedicle screw can be referred to as a "donut collar" in that it is somewhat donut-shaped, surrounding a center of the driving head which includes the hexagonal recess or other torque receiving structure therein. Uniquely with this embodiment relative to other embodiments (described below), the donut collar is fixed to other portions of the head, rather than being rotatable relative to central portions of the driving head which are permanently fixed to the threaded shaft.

The head of the pedicle screw is truncated along a plane of swivel. In one embodiment, this plane of a swivel is adjacent to the hexagonal recess or other torque receiving structure. The plane of swivel is preferably parallel with (or nearly parallel with) the Z-axis along which the threaded shaft of the pedicle screw extends. The plane of swivel is preferably offset away from the Z-axis at least by a radius of the hexagonal recess or other torque receiving structure. In one embodiment, this offset could be greater than a minimum amount with the plane of swivel adjacent to the torque receiving recess or other structure. As one option, a 5 mm offset from the Z-axis is provided at a point on the plane of swivel closest to the hexagonal recess. If the plane of swivel is oriented non-parallel with the Z-axis, such offset is still provided so that the hexagonal recess is spaced from the plane of swivel.

A junction is provided at a proximal end of a spine rod, which junction pivotably attaches to the head of the pedicle screw. The junction has a flat face aligned with the plane of swivel. A swivel post extends perpendicular to the plane of swivel and the flat face of the junction and either extends into the junction or extends into the head of the pedicle screw (or both). This post extends along a swivel axis perpendicular to the plane of swivel and allows for the spine rod to pivot about this swivel access and about the post. Typically, this post is located slightly below the hexagonal recess. The post preferably holds the spine rod to the pedicle screw, but allows the spine rod to swivel relative to the pedicle screw. This swiveling motion can be locked out to fix the spine rod to the pedicle screw without rotation, by tightening a set screw or engaging some other form of lock between the head and the junction.

In one embodiment, a set screw is provided on the donut collar or other periphery of the head, with the set screw generally having a rotational axis parallel to the Z-axis, and with this rotational axis of this swivel set screw offset from the plane of swivel a small amount, such as a similar offset distance as the hexagonal recess is offset from the plane of swivel, in one example embodiment. The swivel set screw resides within a threaded recess, so that male threads on the swivel set screw engage female threads on the recess, to allow the swivel set screw to be tightened down or loosened up within this recess. One end of the swivel set screw has a torque receiving structure therein (such as a hexagonal driver recess).

A second end of the swivel set screw defines a free tip. This free tip in one embodiment is conical in form and abuts a beveled tip of a sliding lock pin which resides within a bore in the head of the pedicle screw. This bore preferably extends perpendicular with the plane of swivel (or at least non-parallel with the plane of swivel) and this bore extends up to the plane of swivel. When the swivel set screw is tightened down, the sliding lock pin is engaged by the free tip of the swivel set screw at the beveled tip of the sliding lock pin and pushed toward the plane of swivel, and then across the plane of swivel into contact with the flat face of the junction of the spine rod portion that is aligned with the plane of swivel. Such engagement between the sliding lock pin and the junction locks the junction and associated spine rod relative to the pedicle screw, so that the overall fixation assembly can be transitioned from a loose first configuration to a tightened and rigid second configuration, where the spine rod and pedicle screw are fixed relative to each other.

A surface of the sliding lock pin opposite the beveled tip can be formed of a harder metal or other material than material forming the junction face, so that the sliding lock pin can embed somewhat into the face of the junction and keep the junction tight and immobile relative to the pedicle screw when the set screw is tightened down onto the sliding lock pin. As other alternatives for a secure engagement, the face of the junction adjacent to the plane of swivel and/or the tip of the sliding lock pin adjacent to the plane of swivel can be roughened, knurled, or otherwise prepared for maximum frictional engagement when the set screw is tightened and the sliding lock pin is slid and held tightly against the junction across the plane of swivel. As a further option, the tip of the sliding lock pin opposite the beveled tip could be fitted with a rubber or other high friction surface to provide sufficient frictional engagement between the spine rod and the pedicle screw to immobilize them relative to each other.

In this all-in-one assembly embodiment, typically the pedicle screw is first placed into a pedicle of a vertebra or other bone of the patient along a desired orientation, defining the Z-axis. This pedicle screw attachment process can be preceded with a drilling step to form a pilot hole if desired. After the pedicle screw has been placed where desired, the spine rod is swiveled about the swivel access until the spine rod has a desired position relative to the pedicle screw. Finally, the swivel set screw is tightened so that the spine rod is immobilized relative to the pedicle screw. If the spine rod needs to be repositioned, the swivel set screw can be loosened, the spine rod swiveled about the post, and the swivel set screw retightened to fix the spine rod in a new position.

The spine rod generally extends away from the junction at a proximal end of the spine rod to a distal end. This distal end could be affixed to other bones of a patient, such as through another pedicle screw affixed to another pedicle. Such a second pedicle screw could attach in the traditional prior art fashion or the distal end of the spine rod could have another junction adjacent to a plane of swivel and another pedicle screw similar to the pedicle screw described above. In such a configuration, the spine rod is initially loosely attached to two separate pedicle screws, one at each end, and with a swivel joint of similar form between each end of the spine rod and the pedicle screws adjacent to the spine rod. The spine rod could have a length similar to a spacing between adjacent vertebrae of a patient, or some multiple of spacing between vertebra of a patient, such that an overall assembly of a spine rod and two pedicle screws could fix adjacent vertebrae together, or span a larger number of vertebrae therebetween, and intermediate pedicle screws could be fastened to intermediate portions of the spine rod between the proximal end and the distal end.

Typically, the spine rod would extend away from the junction at an acute angle away from the plane of swivel, and with the spine rod extending neither parallel with the plane of swivel nor perpendicular to the plane of swivel. Such an acute angle offsetting the spine rod away from the plane of swivel could in one embodiment be about 30°. In other embodiments, acute angles of different measurements could be provided. A user could select from multiple choices of spine rod and pedicle screw all-in-one assemblies having an angular offset of the spine rod away from the plane of swivel which matches the desired angular offset for optimal use by a spinal surgeon.

In a second embodiment disclosed herein, an assembly is provided which has two degrees of freedom. This second embodiment is similar to the first embodiment described above, except that the donut collar of the head of the pedicle screw is not permanently affixed and/or formed with other portions of the head of the pedicle screw. Rather, the driving head of the pedicle screw is at a center of the donut collar, and the donut collar rotates (or floats) relative to the driving head of the pedicle screw. The donut collar is typically formed of similar material as the driving head, such as a surgical stainless steel. The donut collar preferably surrounds at least a majority of the driving head of the pedicle screw, and the donut collar is free to rotate about the Z-axis, so that the post joining the spine rod and junction to the donut can be rotated to different positions relative to the driving head and threaded shaft of the pedicle screw. In one embodiment, the donut collar entirely surrounds the driving head of the pedicle screw, and the truncated plane defining the plane of swivel is spaced at least slightly away from the driving head of the pedicle screw. In a second alternative, the truncated plane is adjacent to the driving head of the pedicle screw, so that the donut collar does not form an entire circuit around the head of the pedicle screw, but extends around somewhat more than half of the driving head of the pedicle screw, such that the donut collar can remain attached to the driving head of the pedicle screw.

In addition to rotation of the donut collar relative to the driving head of the pedicle screw, the donut can also float somewhat, such that a plane in which the donut is centered can be either aligned or unaligned (at least somewhat, such as perhaps up to) 30° away from a plane in which the driving head of the pedicle screw is oriented, such plane of the driving head of the pedicle screw generally being perpendicular to the Z-axis of the pedicle screw, extending along the threaded shaft of the pedicle screw. The donut collar is preferably captured to the driving head, such as by residing within a perimeter annular groove or recess in the driving head.

The donut collar has a radial bore passing at least partially radially from a lateral exterior to an interior adjacent to the driving head of the pedicle screw. This bore has female threads therein and a donut threaded pin with corresponding male threads resides within this bore. Tightening of the donut threaded pin causes the donut collar to be affixed relative to the driving head of the pedicle screw. Correspondingly, loosening of the donut threaded pin allows for the donut collar to rotate (and optionally also float) about the Z-axis of the pedicle screw (and optionally also pivot somewhat relative to the plane of the driving head) for optimal relative positioning. While the bore in which the donut threaded pin is oriented could be within the driving head plane, this hole could also have a central axis not exactly parallel with the driving head plane, provided that the donut threaded pin can engage a perimeter of the driving head of the pedicle screw and exert sufficient force between the donut collar and driving head of the pedicle screw to fix them together.

In one embodiment, the donut collar has a central hole that is too small for the driving head of the pedicle screw to pass through. In such a configuration, the donut collar can move axially along the Z-axis away from the driving head (and potentially even off of the pedicle screw entirely). Such axial adjustability can aid in positioning the pedicle screw and the donut collar precisely where desired.

The donut threaded pin can have at least an engagement tip configured, such as described above relative to the sliding lock pin, for optimal secure fixation of the donut collar to the driving head. A driving tip provided opposite an engagement tip of the threaded pin can be provided with a hexagonal recess or other torque receiving structure. In one embodiment, the donut threaded pin has a hexagonal recess similar in size to a hexagonal recess for engaging the swivel set screw, and with this hexagonal recess also optionally being a similar size within the driving head of the pedicle screw for driving of the pedicle screw. With such a common arrangement, a single (or two) torque applying tool, such as an allen wrench, can engage each of the three (or more) hexagonal recesses as desired for pedicle screw placement and for locking of the various parts of the fixation assembly from an initial configuration with two degrees of freedom to a final configuration with no relative movement between associated parts. Before fixation of the donut collar to the driving head, the donut collar would be rotated and otherwise optimally pivoted to an optimal position and orientation relative to the pedicle screw. The donut threaded pin would then be tightened to prevent further motion between the donut collar and the pedicle screw.

In a third embodiment, three degrees of freedom are provided between similar parts of the fixation assembly as disclosed above. Two of the three degrees of freedom would be the swiveling and donut collar rotation/tilting describe in detail above. This third degree of freedom would be between the spine rod distal end and the junction. In particular, the spine rod portion includes a rotary joint. An axle on one part of the joint extends into a blind bore in the other part of this joint. The axle and blind bore both extending generally along a long axis of the spine rod. A lateral threaded bore and threaded pin allow for selective locking/unlocking of this rotary joint, similar to the donut threaded pin. The distal end of the spine rod can thus rotate relative to the junction (and optionally also translate linearly along a central axis of the spine rod, at least a small amount for length adjustment in one embodiment).

Rotation of the spine rod relative to the junction at this rotary joint, and providing this third degree of freedom, can be beneficial in multiple instances. For instance, if a distal end of the spine rod is fitted with a similar pedicle screw and donut collar and junction as that described above in any of the prior embodiments for the proximal end of the spine rod, such a rotation of the spine rod relative to the junction at this receptacle allows for desired alignment of the two pedicle screws at opposite ends of the spine rod relative to each other. In other embodiments, the spine rod might not be linear, so that rotation of the spine rod relative to the junction allows for optimal orientation of contours of the spine rod relative to anatomy of the patient. Limited translation between the junction and the distal end of the spine rod, if provided, similarly allows for optimal positioning of the pedicle screw and spine rod to provide an optimal fixation assembly.

In use, once the pedicle screws have been secured to bone, the various degrees of freedom are manipulated to position a spine rod where desired relative to the pedicle screws. Various set screws are then engaged with a torque applying tool to tighten them down, so that the spine rod is fixed relative to the pedicle screws and an overall fixation assembly without any remaining degrees of freedom or other flexibility is established. Because the donut collar does not extend (or only slightly extends) beyond the driving head of the pedicle screw along the Z-axis, and because the junction is lateral to this donut collar (or head), and the rotary joint is also lateral to this junction, no portions of the fixation assembly extend appreciably along the Z-axis beyond the driving head of the pedicle screw. In this way, an exceptionally low profile and yet multiple degree of freedom fixation assembly is provided, which avoids or minimizes engagement with adjacent musculature of the patient, and which can generally provide rounded and smooth surfaces to minimize tissue trauma.

If the head also includes a threaded bore extending along the Z-axis, other assemblies can be attached thereto, such as turndown screws and associated tulip heads. Double tulip head assemblies can be utilized to allow for progressive expansion of a fixation assembly, such as to treat scoliosis.

OBJECTS OF THE INVENTION

Accordingly, a primary object of the present invention is to provide a medical implant which has both the characteristics of a pedicle screw and the characteristics of a spine rod in a single assembly.

Another object of the present invention is to provide a hybrid spinal rod and pedicle screw which is lower profile, especially in a dorsal direction, relative to separate spine rod and pedicle screw implants or medical devices.

Another object of the present invention is to provide a hybrid spine rod and pedicle screw which maintains various different degrees of freedom, including up to three degrees of freedom between the spine rod and pedicle screw.

Another object of the present invention is to provide an implantable medical device which can be implanted to stabilize the spine or other bones of a patient, and can be later augmented by attachment of further implantable medical devices to the original implanted medical devices, while maintaining a relatively low profile.

Another object of the present invention is to provide a hybrid spine rod and pedicle screw which facilitates spinal fusion procedures of a wide variety of forms.

Another object of the present invention is to provide a hybrid spine rod and pedicle screw assembly which can be used either percutaneously or subcutaneously.

Another object of the present invention is to provide a hybrid spine rod and pedicle screw assembly and associated method for treatment of scoliosis.

Other further objects of the present invention will become apparent from a careful reading of the included drawing figures, the claims and detailed description of the invention.

DESCRIPTION OF THE PREFERRED EMBODIMENT

Figures 1, 2:
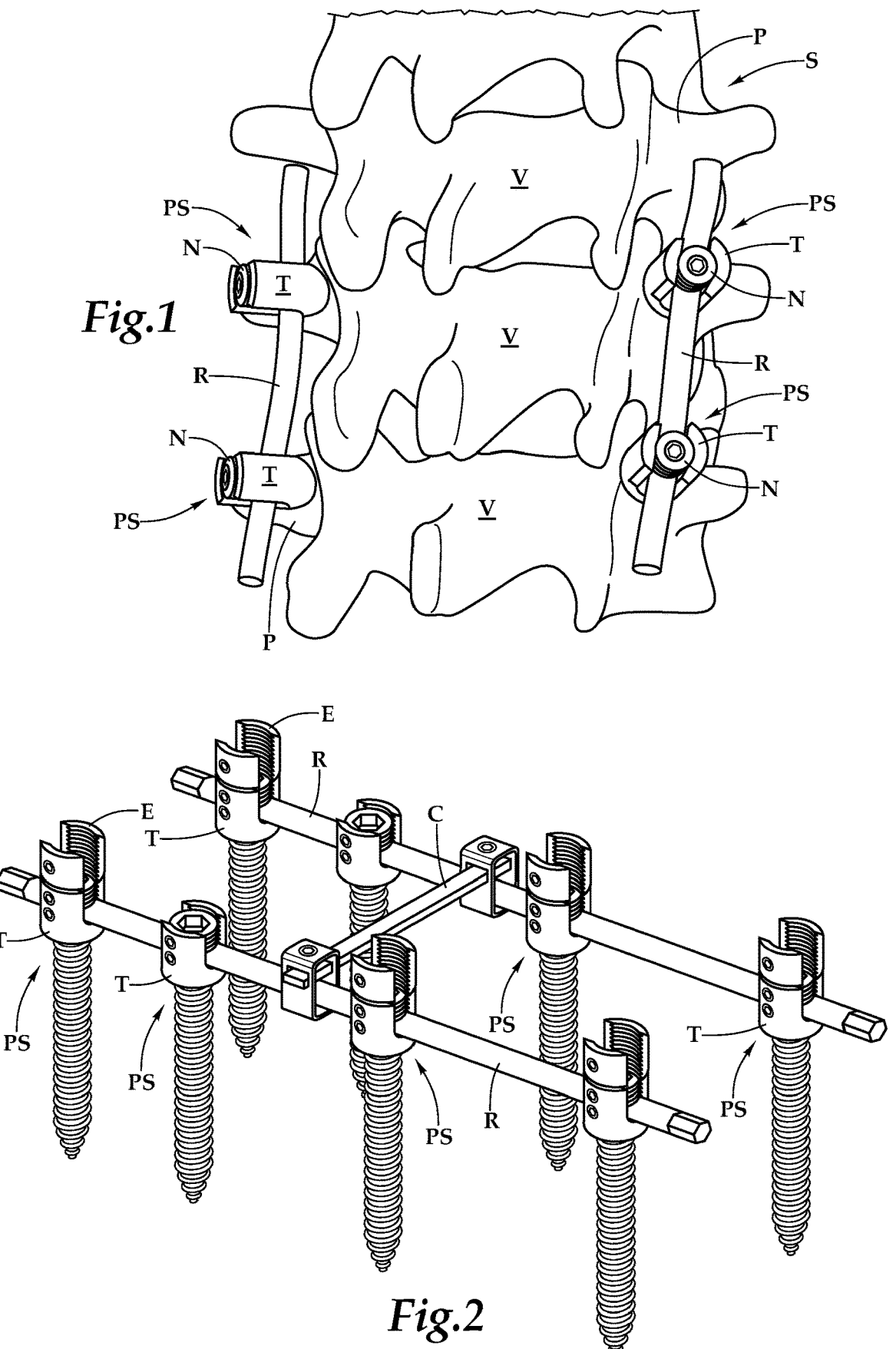
FIG. 1 is a perspective view of a portion of a human spine with a pair of prior art spine rods and pedicle screws provided as assemblies on posterior lateral portions of the spine.
FIG. 2 is a perspective view of a series of prior art pedicle screws with associated tulip heads and spine rods and crosslinks, all attached together according to the prior art.

Referring to the drawings, wherein like reference numerals represent like parts throughout the various drawing figures, reference numeral 10 is directed to a hybrid fixation assembly which combines a pedicle screw portion 12 with a spine rod 40 portion. The resulting hybrid assembly 10 has a low profile and is configured for expansion and interconnection with other bone fixation hardware with a high degree of flexibility and utility.

In essence, and with particular reference to FIGS. 1-8, basic details of the assembly 10 of this invention are described, according to an example embodiment and variations thereof. Assembly 10 includes a pedicle screw portion 12 that itself is comprised of a head 20 and a threaded shaft 30. The threaded shaft 30 extends along a rotational axis Z, with the head 20 at an end thereof. A spine rod 40 is attached to the head 20 at a junction 42 thereof in a manner which facilitates swivel (about arrow B), between the spine rod 40 and head 20 of the pedicle screw portion 12. Set screw 50 is provided to lock the spine rod 40 relative to the head 20, such as after a desired position for the spine rod 40 relative to the head 20 has been achieved and no further motion is desired.

In at least some embodiments, a rotary joint 60 (FIG. 8) can be provided to facilitate rotation of the spine rod 40, especially when the spine rod 40 is non-linear, so that a distal end 43 of the spine rod 40 opposite the junction 42 at the proximal end can be repositioned as desired. A donut collar 70 is provided in one embodiment (FIGS. 6-8), which facilitates pivoting of the donut collar 70 and spine rod 40 about the rotational axis Z. A turndown screw 80 is depicted (FIGS. 9-12) which can support a tulip head 90 (FIGS. 16-19) to allow for attachment of spine rods R to such turndown screws 80, and which turndown screws 80 can attach to the head 20 of the assembly 10, to facilitate extending orthopedic support hardware beyond merely utilization of the assembly 10, either during initial placement or as a later expansion procedure. Such extensions are also facilitated by a first alternate assembly 100 and a double tulip head assembly 200.

Figures 3, 4, 5:
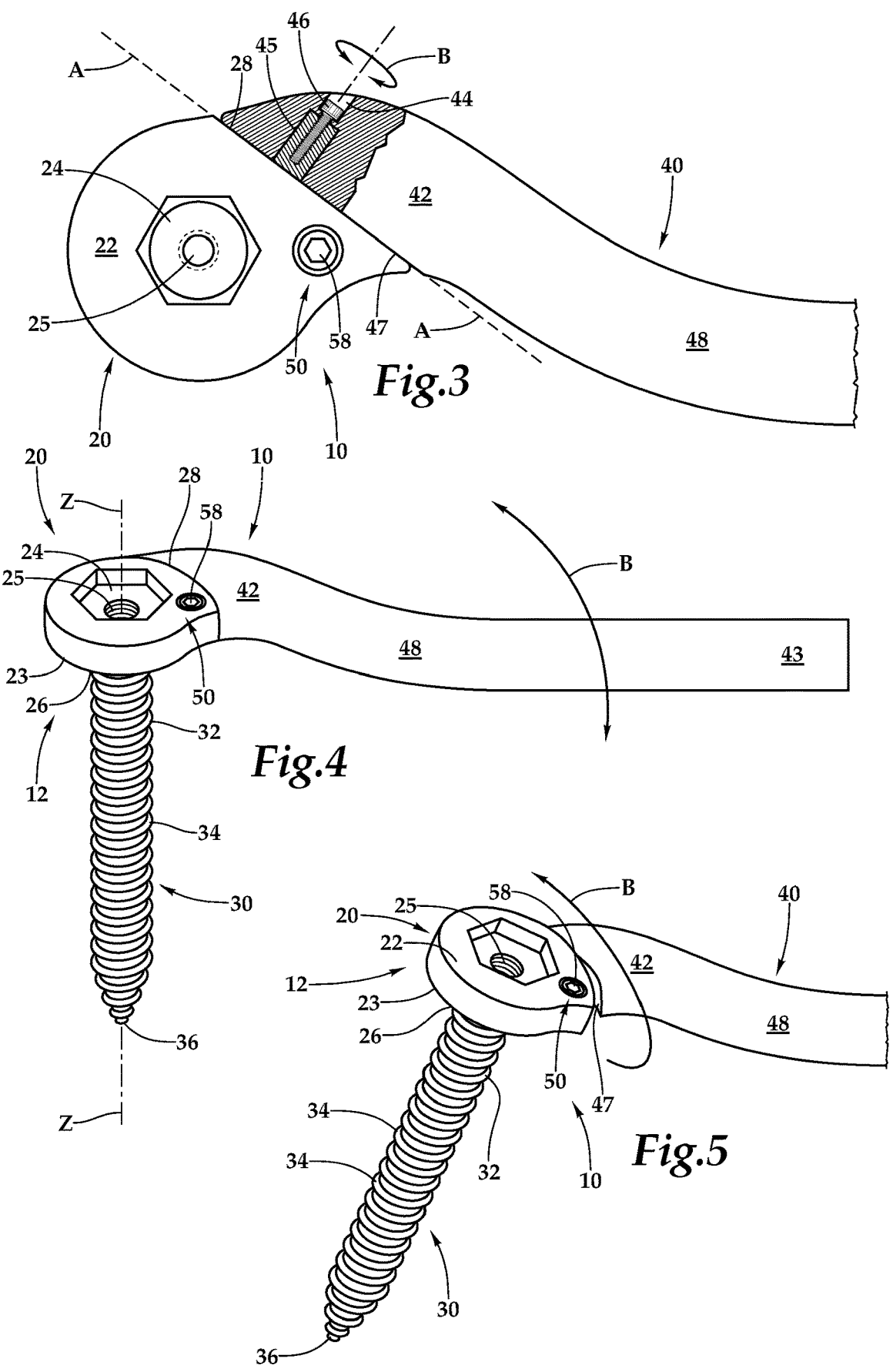
FIG. 3 is a top plan view of a hybrid pedicle screw and spine rod assembly according to a first example embodiment of this invention.
FIG. 4 is a perspective view of that which is shown in FIG. 3.
FIG. 5 is a perspective view of that which is shown in FIG. 4, but after swiveling of a spine rod portion of the assembly somewhat relative to a pedicle screw portion of the assembly.

More specifically, and with particular reference to FIGS. 3-5, details of the assembly 10 according to a first embodiment featuring a single degree of freedom is described. The assembly 10 is configured to provide the benefits of both a pedicle screw PS and a spine rod R (FIGS. 1 and 2) in a single assembly 10. Not only are the benefits of a smaller number of parts enjoyed by this assembly 10, but also a lower profile is provided, especially in a dorsal (rearward) direction relative to utilization of prior art pedicle screws PS and spine rods R held together through tulip heads T, nuts N, extensions E and cross-links C (FIG. 2). Furthermore, ongoing expansion of spine S stabilization hardware configurations is facilitated.

The pedicle screw portion 12 includes the head 20 and threaded shaft 30. In this first embodiment assembly 10 and according to a first and simplest variation, the head 20 and threaded shaft 30 are fixed together as a single structure. They can either be formed together from a unitary mass of material or permanently attached together.

The head 20 has an upper surface 22 opposite a lower surface 23, with the upper surface 22 approximately flat (but potentially with some curving, especially near a perimeter thereof), and with the lower surface 23 typically being at least somewhat semi-spherical. Other geometries for the surfaces 22, 23 could be provided in alternative embodiments. The upper surface 22 features a hex recess 24 as one form of torque receiving structure that extends down into this upper surface 22 somewhat. This hex recess 24 could alternatively be some other form of faceted driver receiving recess (e.g. with more or less than six lateral facets/walls), or potentially a faceted protuberance, which would be fashioned for receipt of a driver tool. This recess 24 allows for torque to be applied to cause the threaded shaft 30 to thread down into bone, such as a pedicle P of a vertebra V of a spine S (FIG. 1).

The head 20 preferably includes a threaded bore 25 at the center of the hex recess 24 and extending vertically along the rotational axis Z. This bore 25 is a blind bore and allows for other structures to be threaded thereinto. These threads are typically "machine threads" in that they have a small difference between major and minor diameters thereof (relative to the bone screw threads of the threaded shaft 30), and a relatively small pitch angle and smaller diameter than a diameter of the threaded shaft 30.

Various items can be threaded thereinto, such as a turndown screw 80 (FIGS. 9-12) or alternate assemblies, such as the first alternate assembly 100 (FIG. 13) described in detail below. In at least some embodiments, this threaded bore 25 could be omitted and basic functionality of the assembly 10 could still be preserved, including attaching to the spine S and holding a spine rod 40 fixed to the spine S through the assembly 10.

The head 20 includes a neck 26 at a central portion of the lower surface 23, where the head 20 transitions into the threaded shaft 30. The threaded shaft 30 includes an upper end 32 adjacent to the neck 26 and extends vertically downwardly to a tip 36. Threads 34 are provided on an exterior surface of a threaded shaft 30. The threaded shaft 30 is generally cylindrical in form. The threads 34 are preferably configured as bone threads having a relatively large difference between major and minor diameters and relatively high pitch angle (compared to the threads of the threaded bore 25). The tip 36 can optionally be configured as a self-tapping tip, such as by including flutes and cutting teeth thereon.

The head 20 includes a facet 28 on a lateral side thereof closest to the spine rod 40 and aligned with a plane of swivel A between the head 20 and the junction 42 at the proximal end of the spine rod 40. Other lateral portions of the head 20 are generally cylindrically curving and causing the head 20 to have a generally flattened cylinder shape. Near a center of this facet 28 a swivel post 45 extends laterally away from the head 20. In this embodiment, the swivel post 45 is formed with or otherwise affixed to the head 20 in a permanent fashion. This swivel post 45 allows for attachment to the spine rod 40 in a manner which holds the spine rod 40 to the head 20, but allows for the spine rod 40 to swivel relative to the head 20 about the swivel post 45 (and about arrow B) and parallel to a plane of swivel A (FIG. 3). As an alternative, the swivel post 45 could be fixed to the spine rod 40 or floating and neither fixed to the head 20 or the spine rod 40.

The spine rod 40 is an elongate rigid structure extending from the junction 42 at a proximal end to a distal end 43 opposite the junction 42. The junction 42 is located adjacent to the facet 28 of the head 20. The distal end 43 is a plain terminus similar to other prior art spine rods R. The spine rod 40 can feature a bend 48 or other contours between the junction 42 and distal end 43 in various embodiments. As an alternative, the spine rod 40 could be perfectly linear as it extends from the junction 42 to the distal end 43.

To facilitate swiveling of the spine rod 40 about the swivel post 45 of the head 20, a bore 44 is provided in a face 47 of the spine rod 40. This bore 44 is sized large enough to allow the swivel post 45 to extend thereinto and facilitate rotation (along arrow B of FIGS. 3-5). This bore 44 in this embodiment passes entirely through the junction 42 end of the spine rod 40 to allow for a capture bolt 46 to thread into the swivel post 45 at a tip thereof, and hold the spine rod 40 to the head 20.

This capture bolt 46 could as an alternative be a rivet or other permanent fastener, as the spine rod 40 in a simplest embodiment, is always attached to the assembly 10 in a non-removable fashion. However, as an option, this capture bolt 46 could be a threaded bolt which could be accessed not only for initial manufacture, but also for potential disassembly, such as to allow for swapping of one spine rod 40 with another spinal rod 40 having different lengths, bends, contours, diameters, or other configurational details. This allows for modification of assembly 10, even after implantation, and without requiring removal of the pedicle screw portion 12 from the pedicle P of the vertebra V.

Both the face 47 of the spine rod 40 and the facet 28 of the head 20 are preferably planar and located adjacent to each other and adjacent to the plane of swivel A, perpendicular to the axis about which swivel occurs (along arrow B). This plane of swivel A can, in one embodiment, be a vertical plane (vertical being defined for this purpose as parallel with axis of rotation Z). In an alternative embodiment, the plane of swivel A could have some (typically small) amount of deviation away from being a fully vertical plane. This plane of swivel A can be offset various different distances away from a Z axis aligned with a center of the threaded shaft 30. In one embodiment this offset is 5 mm. Assemblies 10 having different offsets could be provided so that a surgeon could select a desired amount of offset for the assembly 10 before attachment. If desired, this offset could be adjusted such as by swapping one spine rod 40 for a different spine rod utilizing the capture bolt 46 and swivel post 45, or by placing a spacer around the swivel post 45 and between the spine rod 40 and head 20 to enhance such spacing.

The assembly 10 allows the spine rod 40 to swivel relative to the head 20, except when a set screw 50 associated therewith has been activated to lock the spine rod 40 relative to the head 20. In particular, the set screw 50 is preferably located accessible from the upper surface 22 of the head 20 and located generally between the hex recess 24 and the facet 28. The head 20 can be provided with a somewhat radially non-symmetrical form that extends a greater distance away from a vertical central axis of the head 20 on portions of the head 20 closest to the distal end 43 of the spine rod 40. This extra space in the head 20 provides a location where the set screw 50 can be accommodated.

In one example embodiment, the set screw 50 has a pointed conical tip 52 and resides within a vertical bore 54 which includes female threads on a cylindrical perimeter thereof. Set screw 50 has male threads which cooperate with these female threads in the vertical bore 54 so the rotation of the set screw 50, by engaging a driver recess 58 in the upper end of the set screw 50, causes the set screw 50 to move up and down within this vertical bore 54.

A horizontal bore 56 accesses an innermost portion of this vertical bore 54. A lock pin 55 resides within this horizontal bore 56. The horizontal bore 56 extends out of the facet 28 of the head 20. The lock pin 55 has a beveled first end 57 located adjacent to the conical tip 52 of the set screw 50. A second end 59 of the lock pin 55 opposite the beveled first end 57 is preferably flat and perpendicular to the center line of the lock pin 55.

The lock pin 55 could be cylindrical or could be of some other cross-section, such as a somewhat square cross-section; in which case the horizontal bore 56 would have a corresponding cross-section. By having a horizontal bore 56 be at least partially non-circular in cross-section, and with the lock pin 55 having a corresponding non-circular cross-section, the beveled first end 57 can be kept with a constant orientation for meeting along a surface or at least a line with the conical tip 52 of the set screw 50. When the set screw 50 is rotated to cause downward motion within the vertical bore 54 (along arrow F of FIGS. 6 and 7), the conical tip 52 interacts with the beveled first end 57 of the lock pin 55 to move the lock pin 55 horizontally (along arrow G of FIG. 7) within the horizontal bore 56 and out of the facet 28, and into the face 47 of the spine rod 40.

Tightening of the set screw 50 causes locking of the second end 59 of the lock pin 55 against the face 47 of the spine rod 40 to lock the spine rod 40 relative to the head 20. Such a locking force can be enhanced by knurling or otherwise roughening the second end 59 and/or by knurling or roughening an arc on the face 47 of the spine rod 40 which is along a path having a distance away from the swivel post 45 similar to a distance that the horizontal bore 56 is away from the swivel post 45. As another option, at least portions of the face 47 can be formed of a softer metal than that from which the lock pin 55 is formed. An angle of the conical tip 52 and an angle of the beveled first end 57 preferably match each other, and are also selected to cause the set screw 50 to be resistant to loosening, such that the spine rod 40 and head 20 can be securely held together unless the set screw 50 is accessed by a torque applying tool within the driver recess 58 thereof to cause loosening of the set screw 50 and re-enabling swivel of the spine rod 40 relative to the head 20.

Figures 6, 7, 8:
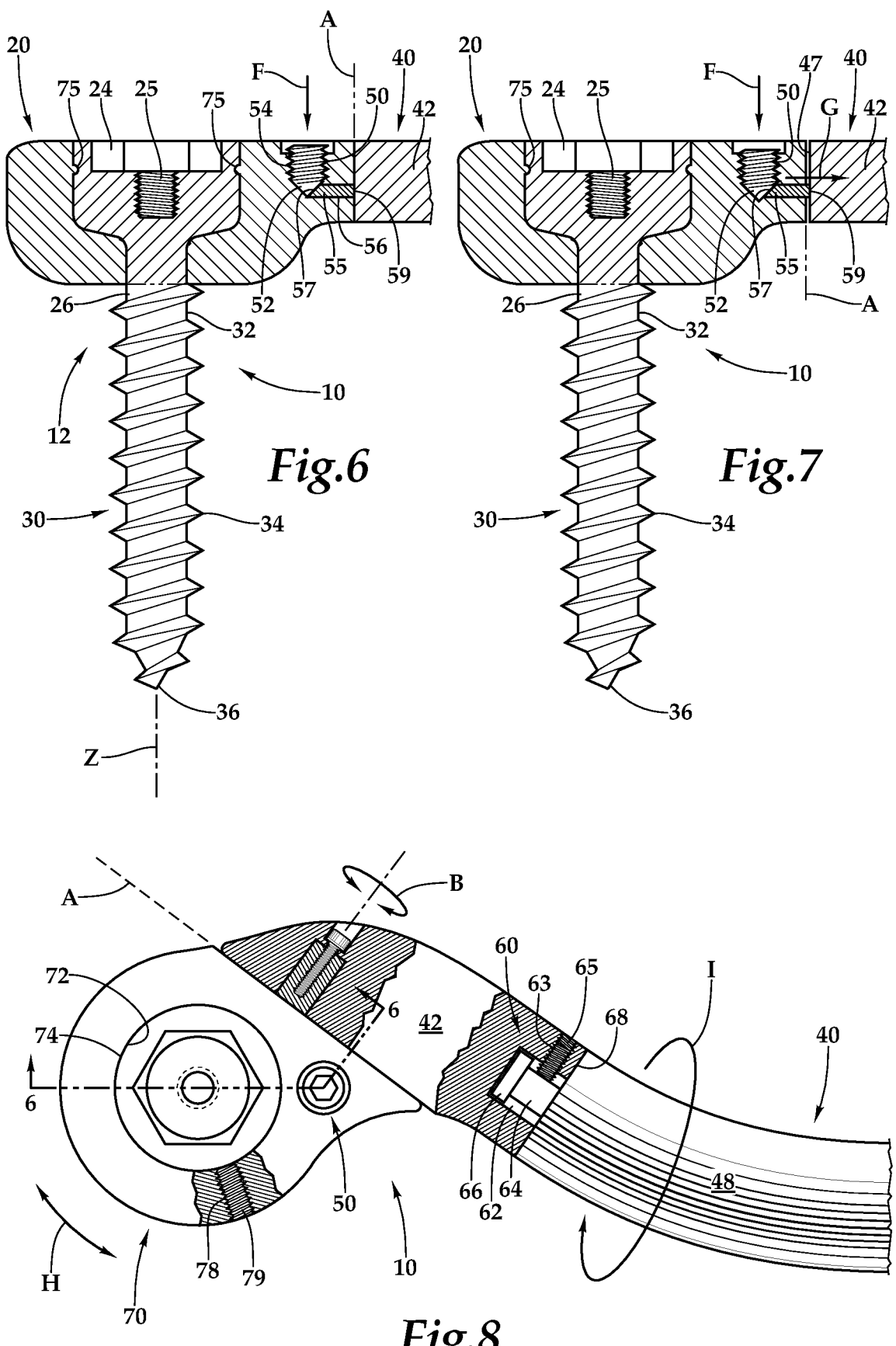
FIG. 6 is a partial sectional elevation view of an alternative embodiment of that which is shown in FIG. 3, that is also shown in FIGS. 7 and 8.
FIG. 7 is a partial sectional elevation view similar to that which is shown in FIG. 6, but after a lock pin thereof has been advanced to lock the spine rod portion of the assembly with the pedicle screw portion of the assembly from relative swivel.
FIG. 8 is a top plan view of that which is shown in FIGS. 6 and 7, and which is a variation of the assembly of FIG. 3, which includes an additional rotating degree of freedom and an additional pivoting degree of freedom between the spine rod portion of the assembly and the pedicle screw portion of the assembly.
Figure 9:
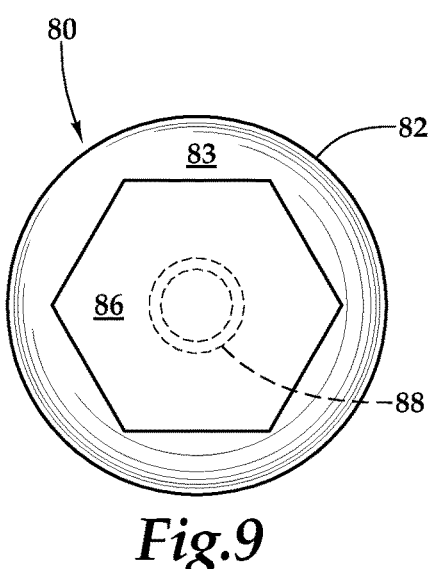
FIG. 9 is a top plan view of a turndown screw which is provided for use within various assemblies according to this invention.
Figure 11:
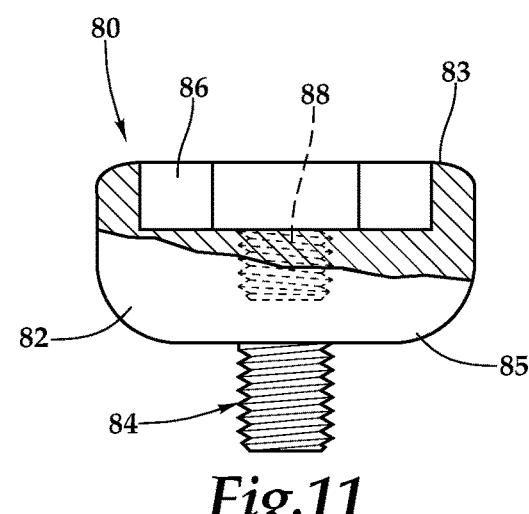
FIG. 11 is a front elevation partial sectional view of that which is shown in FIG. 9.
Figure 10:
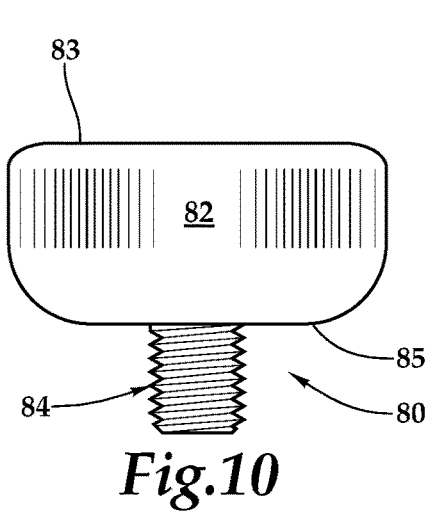
FIG. 10 is a front elevation view of that which is shown in FIG. 9.
Figure 12:
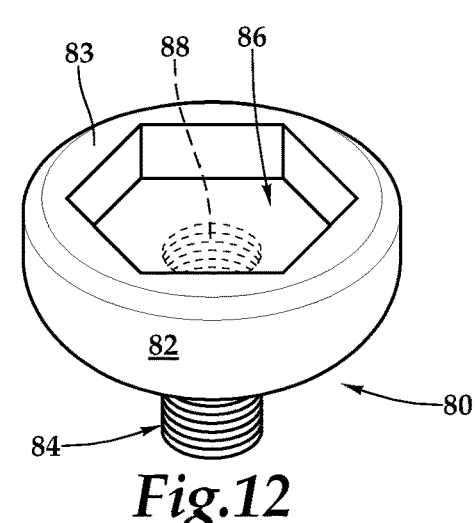
FIG. 12 as a perspective view from above of that which is shown in FIG. 9.

FIGS. 6 and 7 depict this action of the set screw 50 and lock pin 55 to cause locking between the head 20 and the spine rod 40. In FIGS. 6 and 7 a variation of the assembly 10 described above is depicted where the head 20 exhibits a donut collar 70. This embodiment featuring the donut collar 70 is also depicted in FIG. 8, which also depicts an optional assembly 10 variation featuring a rotary joint 60 for the spine rod 40.

The rotary joint 60 allows for the distal end 43 of the spine rod 40 to be rotated relative to the junction 42 at a proximate end of the spine rod 40. The rotary joint 60 is provided by splitting the spine rod 40 into a proximal portion and a distal portion, which come together at bearing surfaces 68. In the example embodiment of the rotary joint, a blind bore 62 is formed in the proximal portion adjacent to the bearing surface 68. An axle 64 extends from the distal portion and is sized to fit within the blind bore 62. A flange 66 is provided at a distal tip of the axle 64.

A lateral threaded bore 63 extends laterally through the proximal portion of the spine rod 40 and accesses the blind bore 62 from a lateral side. A threaded pin 65 can pass through this lateral threaded bore 63 and beneath the flange 66 to hold the distal portion of the spine rod 40 to the proximal portion of the spine rod 40 at the bearing surfaces 68 thereof. When the threaded pin 65 is loosened, the distal portion of the spine rod 40 can be rotated (about arrow I of FIG. 8) relative to the proximal portion of the spine rod 40. This is especially useful when the spine rod 40 includes a bend 48 therein, so that the distal end 43 of the spine rod 40 can be positioned in various different locations by utilizing the rotary joint 60.

With continuing reference to FIG. 8 (as well as FIGS. 6 and 7), details of the donut collar 70 are described, which facilitate pivoting motion about the threaded shaft 30 rotational axis Z, extending along the threaded shaft 30 between the head 20 and the donut collar 70. With this donut collar 70 variation, the head 20 is split into a central driver head portion and a perimeter portion referred to as the donut collar 70. The donut collar 70 pivots (along arrow H of FIG. 8) relative to the driver head to provide a further degree of freedom for the assembly 10, between the pedicle screw portion 12 and the spine rod 40.

The donut collar 70 includes an inner race 72 adjacent to an outer race 74, with the inner race 72 on the donut collar 70 and the outer race 74 on the inner central driver head portion of the head 20. If desired, a circumferential groove 75 (and corresponding rib) can be provided within these races 72, 74 to help to keep them aligned and limit relative motion to motion about the axis Z (FIGS. 4 and 6) extending along the threaded shaft 30. As an alternative to the groove 75, the races 72, 74 could be semi-spherical and accommodate some wobble of the driver head relative to the donut collar 70.

A perimeter 76 of the donut collar 70 outboard of the inner race 72 has a radial threaded bore 78 passing laterally therethrough, on a portion of the donut collar 70 spaced away from the spine rod 40. A threaded pin 79 rotates within this radial threaded bore 78 and can be tightened down against the inner central driver portion of the head 20 and against portions of the outer race 74 to allow for locking up the donut collar 70 relative to the inner portions of the head 20, and to lock out this additional pivoting degree of freedom otherwise provided by the donut collar 70. Between the pivoting donut collar 70, rotary joint 60 and swivel post 45, three different rotational degrees of freedom are provided for the assembly 10, when all of the variations of this assembly 10 are provided, such as in the embodiment depicted in FIG. 8. Other details of this assembly 10 featuring the donut collar 70 will be similar to those described above with respect to FIGS. 3-5.

Figure 13:
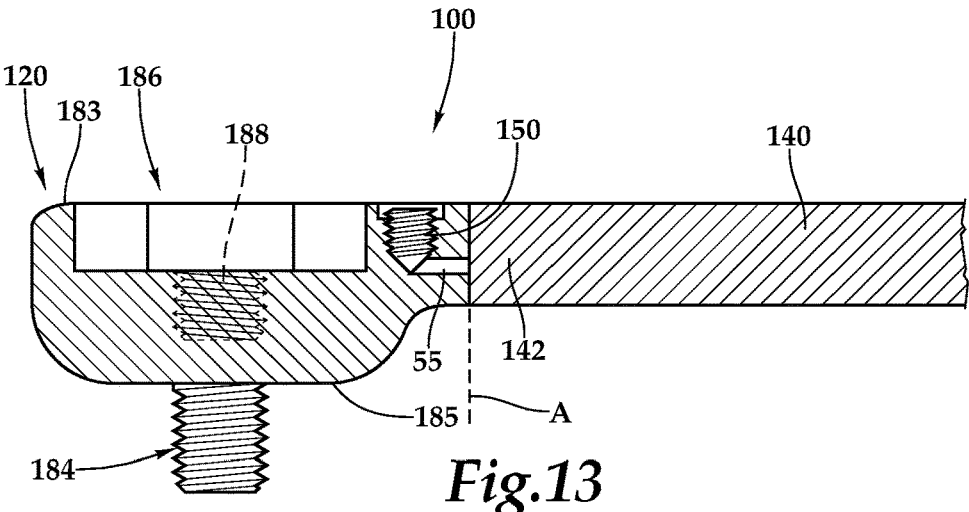
FIG. 13 is a sectional front elevation view of an alternative embodiment of that which is shown in FIG. 3 and featuring a short shaft with fine threads thereon, the short shaft extending vertically rather than a threaded shaft with bone threads thereon, as is the case with the embodiment of FIGS. 4-7.

With particular reference to FIGS. 9-12, details of a turndown screw 80 are described, according to one example embodiment. The turndown screw 80 can work with a tulip head 90 (FIGS. 16-23) or can be provided as a substitute for the pedicle screw portion 12 in a first alternate assembly 100 (FIG. 13). The turndown screw 80 is in many ways similar to the head 20 of the assembly 10, except without the set screw 50 and without the spine rod 40 attached laterally thereto (although this is an option with the assembly 100 shown in FIG. 13).

The turndown screw 80 includes a body 82 of generally cylindrical form with a greater diameter than a height. A short shaft 84 extends vertically downwardly from a center of this body 82 on a bottom surface 85 thereof, opposite of the top surface 83. A faceted recess 86 is provided within the top surface 83. This faceted recess 86 is in one embodiment the same size and configuration as the hex recess 24 of the head 20. In other embodiments, other configurations can be provided for this faceted recess 86 to receive a torque applying tool and cause rotation of the turndown screw 80 about a vertical axis aligned with the short shaft 84. The short shaft 84 is threaded, but typically threaded with find machine threads rather than bone threads. The short shaft 84 is particularly provided with threads and a diameter which can fit within the threaded bore 25, which extends into a floor of the hex recess 24 of the head 20 (FIGS. 3-8).

The turndown screw 80 can optionally include a threaded bore 88 extending vertically downward into a floor of the faceted recess 86 located in the top surface 83 of the turndown screw 80. In this way, multiple turndown screws 80 could be threadably attached to each other as one option. Other devices with a threaded bore of appropriate size could also be threadably attached into such an optional threaded bore 88 (such as assembly 100 of FIG. 13), if such a threaded bore 88 is provided within this turndown screw 80.

In one embodiment (FIG. 13) a turndown screw 80 has its body 82 augmented to include a set screw 50 and spine rod

Figures 14, 15:
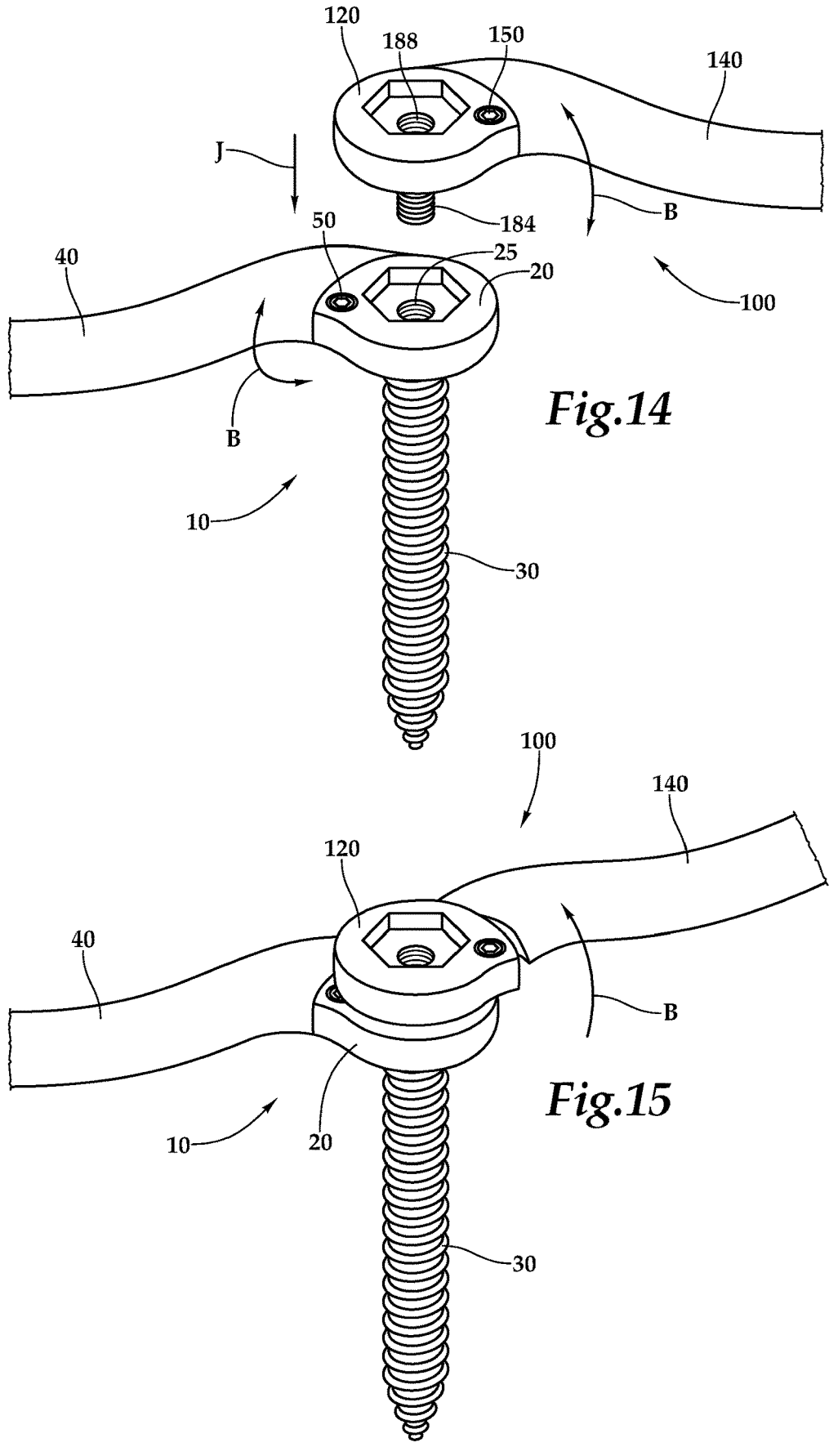
FIG. 14 is a perspective view of the assembly of FIG. 13 exploded away from the assembly of FIGS. 3-5, and illustrating how these two assemblies can be removably attached together in one configuration according to this invention.
FIG. 15 is a perspective view of that which is shown in FIG. 14 and with the two assemblies fully joined together.
Figures 16, 17, 18, 19:
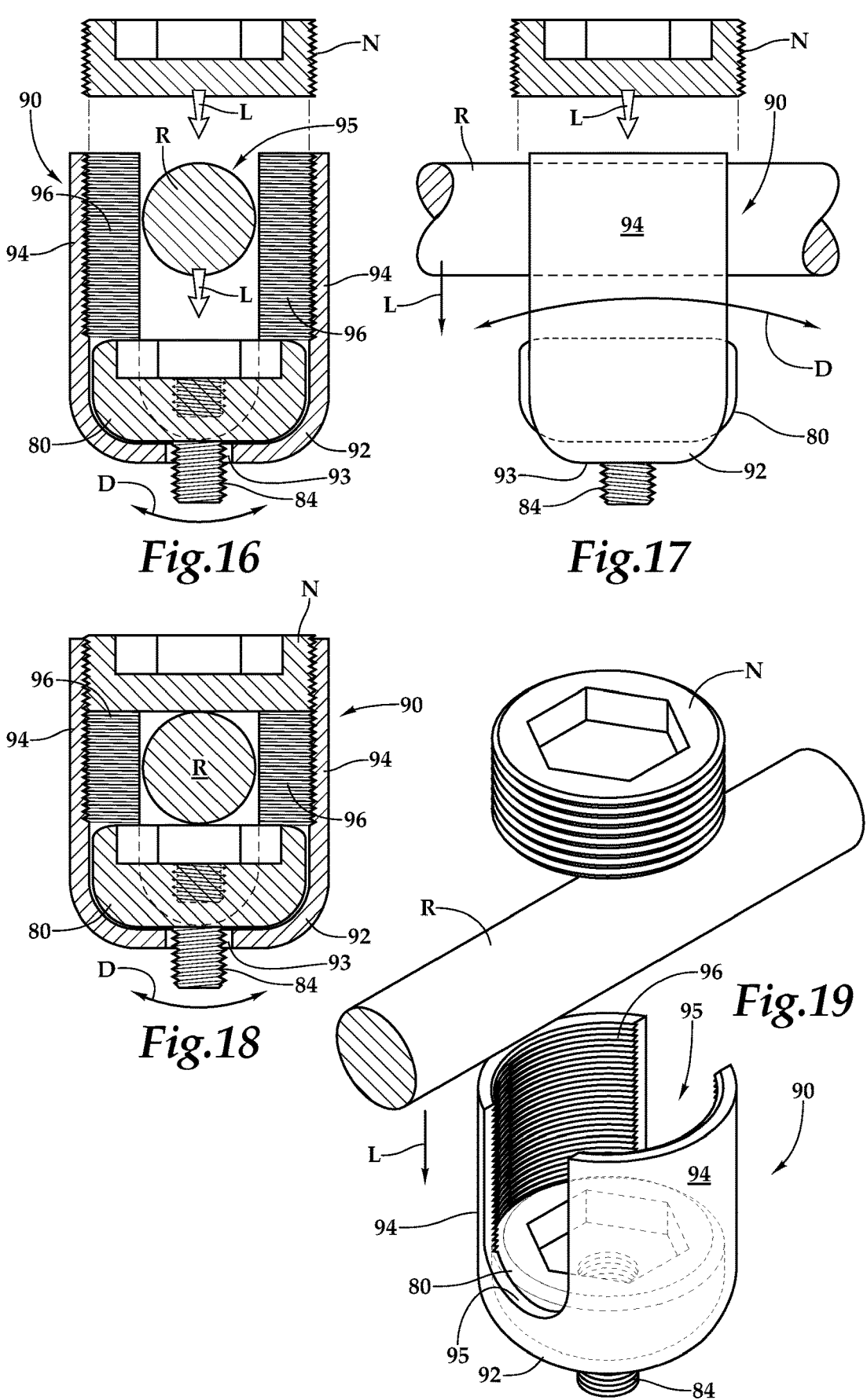
FIG. 16 is a side elevation view of the turndown screw of FIGS. 9-12 and also featuring a tulip head and showing how a spine rod and nut work with the tulip head to hold the spine rod to the turndown screw.
FIG. 17 is a front elevation view of that which is shown in FIG. 16.
FIG. 18 is a perspective view of that which is shown in FIGS. 16 and 17, after full assembly of the turndown screw, tulip head, spine rod and nut.
FIG. 19 is a perspective exploded view of that which is shown in FIGS. 16-18.

40 joining together at a plane of swivel A, so that a first alternate assembly 100 is provided. This first alternate assembly 100 can be identical to the assembly 10 in its various forms, such as those depicted in FIG. 3-8, except that the threaded shaft 30 is replaced with the short shaft 84 associated with the turndown screw 80. Such a first alternate assembly 100 can then be threadably attached into the threaded bore 25 within the head 20 of the assembly 10 to allow for stacking attachment of multiple assemblies 10, 100 together (see arrow J of FIGS. 14 and 15).

With particular reference to FIGS. 16-19 details of a tulip head 90 are described, according to one example embodiment, which can be utilized along with the turndown screw 80 to allow for a prior art spine rod R (or spine rod portion 40 of an assembly 10, 100) and associated nut N to interact. To hold the spine rod R to the turndown screw 80 (which would typically be threaded into the threaded bore 25 in the head 20 of one of the assemblies 10 describe in detail above), the tulip head 90 is provided. This provides another methodology by which prior art spine rods R can be attached to the assemblies 10 describe in detail above.

The tulip head 90 includes a base 92 with a hole 93 extending vertically up through a bottom thereof. This hole 93 is sized to allow the short shaft 84 of the turndown screw 80 to pass through. Furthermore, this hole 93 is preferably oversized to allow for pivoting of the tulip head 90 somewhat relative to turndown screw 80, when they are attached together (along arrow D of FIGS. 16-18). An upper surface of the base 92 is preferably semi-spherical and interacts with the semi-spherical bottom surface 85 of the turndown screw 80, which is also slightly smaller than inner dimensions of the tulip head 90 to facilitate pivoting and surface contact at a variety of different pivot angles between the tulip head 90 and turndown screw 80. The tulip head 90 thus acts as a poly axial tulip head in one embodiment. Alternatively, the hole 93 can be sized just slightly larger than the short shaft 84 so the tulip head 90 would not be pivotable relative to the turn down screw 80.

A pair of petals 94 extend vertically upward from the base 92 with slots 95 between the petals 94. The slots 95 are large enough to allow a spine rod R to fit therein. The petals 94 have thread segments 96 on inner surfaces thereof which interact with threads of the nut N. The nut N can thus drop into these thread segments 96 in the petals 94 and tighten down (along arrow L of FIGS. 16, 17, 19 and 20) onto a spine rod R to hold it against the top surface 83 of the turndown screw 80 and hold the entire assembly including the nut N to tulip head 90, spine rod R and turndown screw 80 (as well as whatever the turndown screw 80 is attached to through the short shaft 84) altogether as a fixed assembly. Attachment of the tulip head 90 to the turndown screw 80 and associated attachment of the spine rod R and nut N to the turndown screw 80 are depicted in FIGS. 16-19, and with potential pivoting of the tulip head 90 shown along arrow D, when the hole 93 is large enough to accommodate such pivoting action.

While the spine rod R is shown as a regular prior art spine rod, it could alternatively be a spine rod 40 associated with the assembly 10 or first alternate assembly 100 in an alternative embodiment of this invention. Threaded bore 25 and threaded bore 88 in the turndown screw 80 can be utilized in at least three different ways. In a first way, it is utilized in an original surgical procedure when pedicle screw portions 12 are placed to allow for stacking attachment of various different assemblies 10, 100 or other implantable medical devices for spine S stabilization. In a second embodiment, these threaded bores 25, 88 are not initially utilized but merely left open. Then, if it is later desired to add further stabilization hardware, such as to adjacent levels of the spine S, these threaded bores 25, 88 are available for attachment of additional hardware. In a third scenario, the threaded bores 25, 88 are initially utilized by hardware throughout attached thereto. Later, it may be desired to remove that hardware. The hardware to be removed is merely unthreaded from these threaded bores 25, 88 and then replacement hardware can optionally be attached thereto. With each of these scenarios significant added therapeutic benefit is provided.

Figures 20, 21:
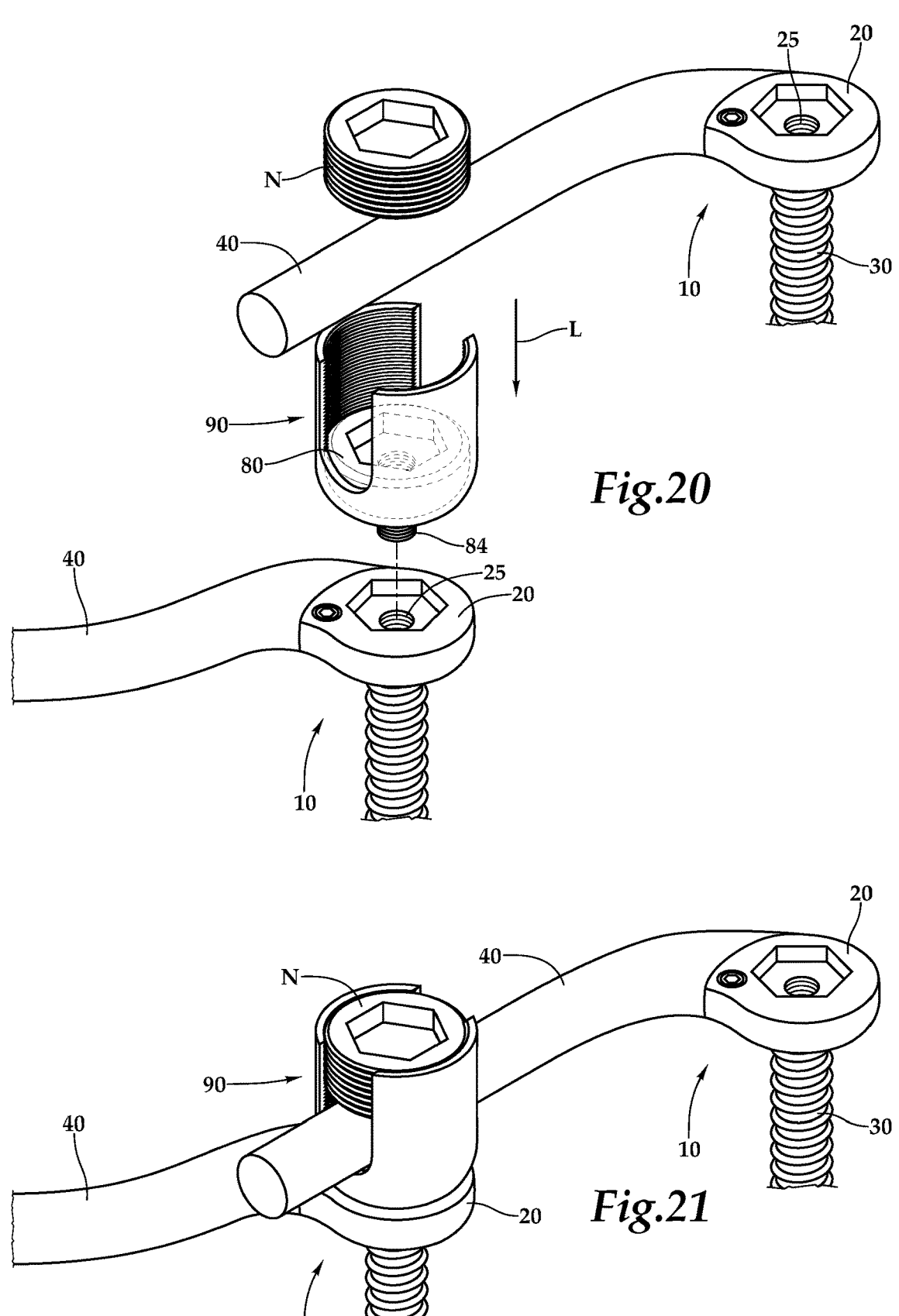
FIG. 20 is an exploded perspective view of a pair of assemblies of FIGS. 3-5 joined together via the turndown screw and tulip head assembly of FIGS. 9-12 and 16-19.
FIG. 21 is a perspective view of that which is shown in FIG. 20 after full assembly.
Figure 22:
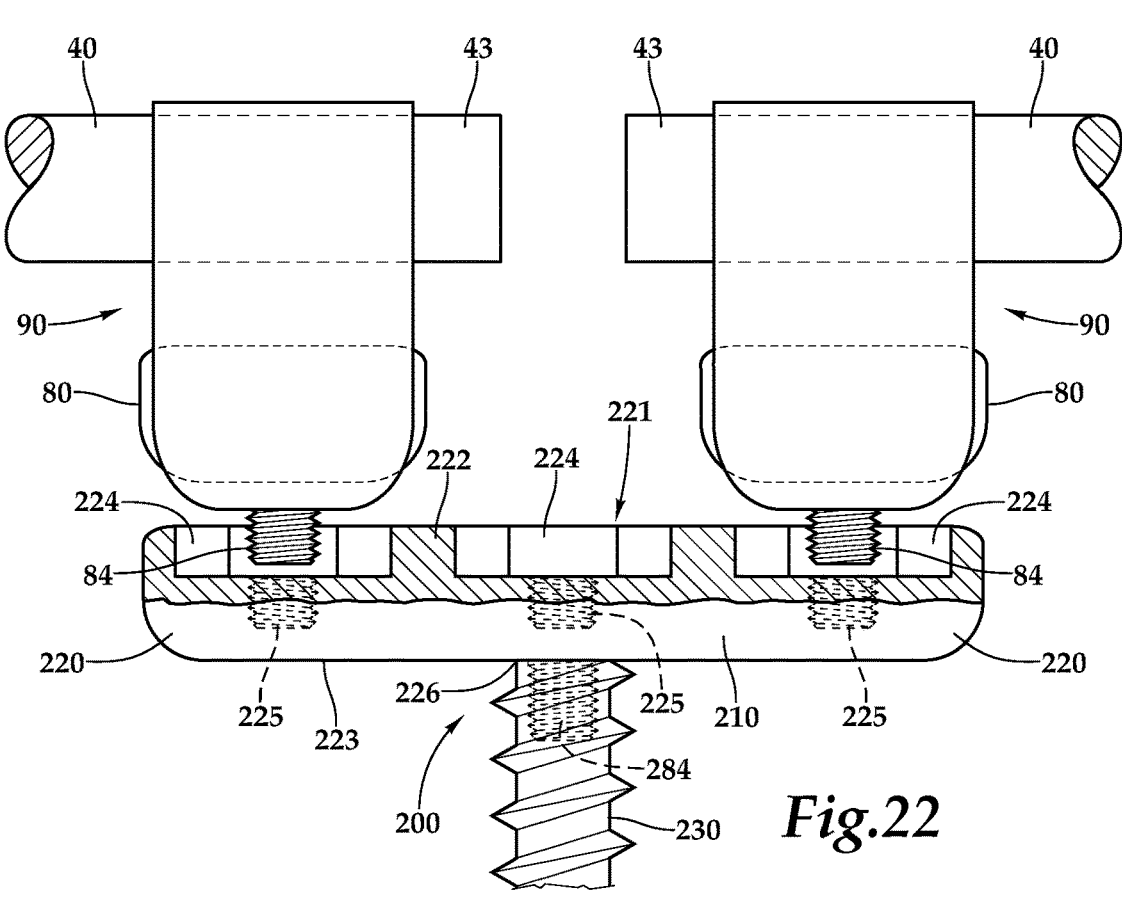
FIG. 22 is a front elevation partially cut away view of a double tulip head assembly with two tulip heads and turndown screws attached to two lateral heads thereof, and with separate spine rods exploded above the tulip heads somewhat.
Figure 23:
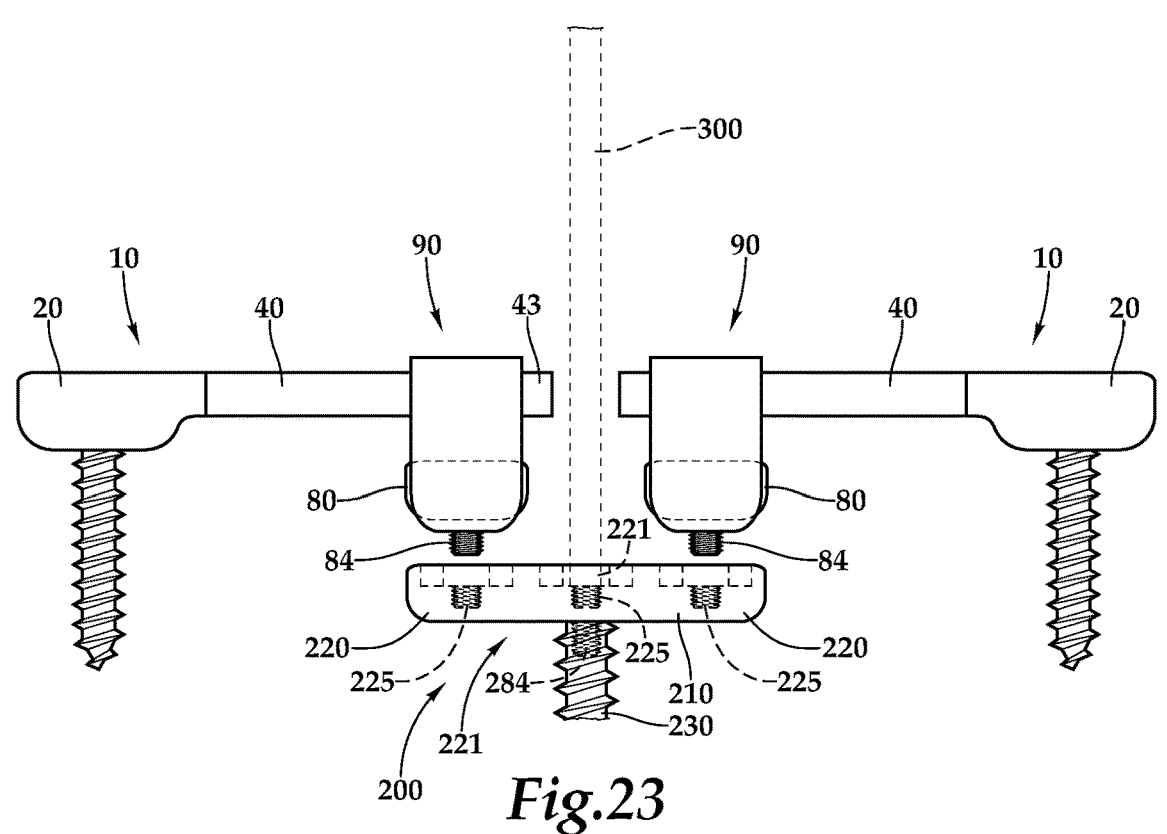
FIG. 23 is a front elevation view similar to that which is shown in FIG. 22, except showing that the spine rods are parts of fixation assemblies including separate pedicle screws, such as those assemblies depicted in FIGS. 3-5, and with a tower shown in broken lines attached to a central threaded bore of the double tulip head assembly.

For instance, and as shown in FIGS. 20 and 21, the tulip head 90 along with the turndown screw 80 can be attached to a head 20 of an assembly 10 (along arrow L). Then a similar second assembly 10 can have a spine rod 40 thereof located within the slots 95 of the tulip head 90. A nut N can thread into the thread segments 96 on the petals 94 of the tulip head 90 and hold the spine rod 40 of one assembly 10 adjacent to the tulip head 90 and turndown screw 80, which is attached to the head 20 of a second assembly 10. In such a way, a series of two or more assemblies 10 can be attached together with each threaded shaft 30 of each new assembly 10 being attached to a separate pedicle P of a next vertebra V of a spine S. No loose spine rods R need to be handled. Rather, the spine rods 40 remain attached to an associated head 20 of an assembly 10.

While assemblies 10 are shown in their simplest embodiment without the donut collar 70 or rotary joint 60, such stacking of multiple assemblies 10 could similarly be achieved with assemblies 10 which feature the rotary joint 60 and/or donut collar 70. With such extra degrees of freedom provided by the rotary joint 60 and/or donut collar 70 it is made more easy to swivel the spine rod 40 of one assembly 10 into the slots 95 of a tulip head 90 attached through a turndown screw 82 of a head 20 of another assembly 10. After such a placement, various set screws 50 and/or threaded pins 65, 79 can be tightened and the nut N can also be tightened to provide final fixation through the multiple assemblies 10 of the associated vertebra V of the spine S.

With particular reference to FIGS. 22-25, a modified pedicle screw is shown in the form of a double tulip head assembly 200. This assembly 200 is configured to have two turndown screws 80 and associated tulip heads 90 attached thereto, as shown. The assembly 200 includes a bar 210 which has a long axis extending horizontally (perpendicular to a rotational axis) and which includes two lateral heads 220 at ends thereof, as well as the central head 221 at a central portion thereof. These heads 220, 221 are merely defined by regions on the bar 210 in the example embodiment. The bar 210 has an upper surface 222 opposite a lower surface 223, which are generally parallel and spaced from each other by a height of the bar 210. In one example embodiment, this bar 210 height is similar to a height of the head 20 of the assembly 10 (FIGS. 3-8) between the upper surface 22 and lower surface 23.

Each of these heads 220, 221 preferably includes a hex recess 224 (although these are optional for at least the lateral heads 220) therein and a threaded bore 225 located centrally within a floor of each hex recess 224. This configuration of the hex recesses 224 and threaded bores 225 within each of the heads 220, 221 can be similar to the orientation of the hex recess 24 and threaded bore 25 within the head 20 of the assembly 10 (FIGS. 3-5). A center of the lower surface 223 defines a neck 226 which transitions into a threaded shaft 230 similar to the threaded shaft 30 associated with the assembly 10. As an alternative to the threaded shaft 230, a short shaft 284 could be provided, similar to the short shaft 84 of the turndown screw 80 and sized to fit within the threaded bores 225 or threaded bores 25, 188 (in at least one embodiment). The threaded shaft 230 facilitates screwing of the double tulip head assembly 200 into a pedicle P of a vertebra V.

Each of the lateral heads 220 preferably has a turndown screw 80 and tulip head 90 attached thereto. This allows the double tulip head assembly 200 to be configured to receive two spine rods R, one within each of the slots 95 of each of the tulip heads 90. The spine rods R could be a standard prior art spine rod R which has portions thereof spaced away from the double tulip head assembly 200 fixed to adjacent vertebra V, such as through prior art pedicle screws PS. However, according to one embodiment of this invention, these tulip heads 90 receive spine rods 40 which are portions of assemblies 10 described in detail above. A tower 300 can attach to the central head 221 through its threaded bore 225. If no hex recess 224 is provided, torque could be applied to the tower to install the double tulip head assembly 200 into a pedicle P.

Figure 24:
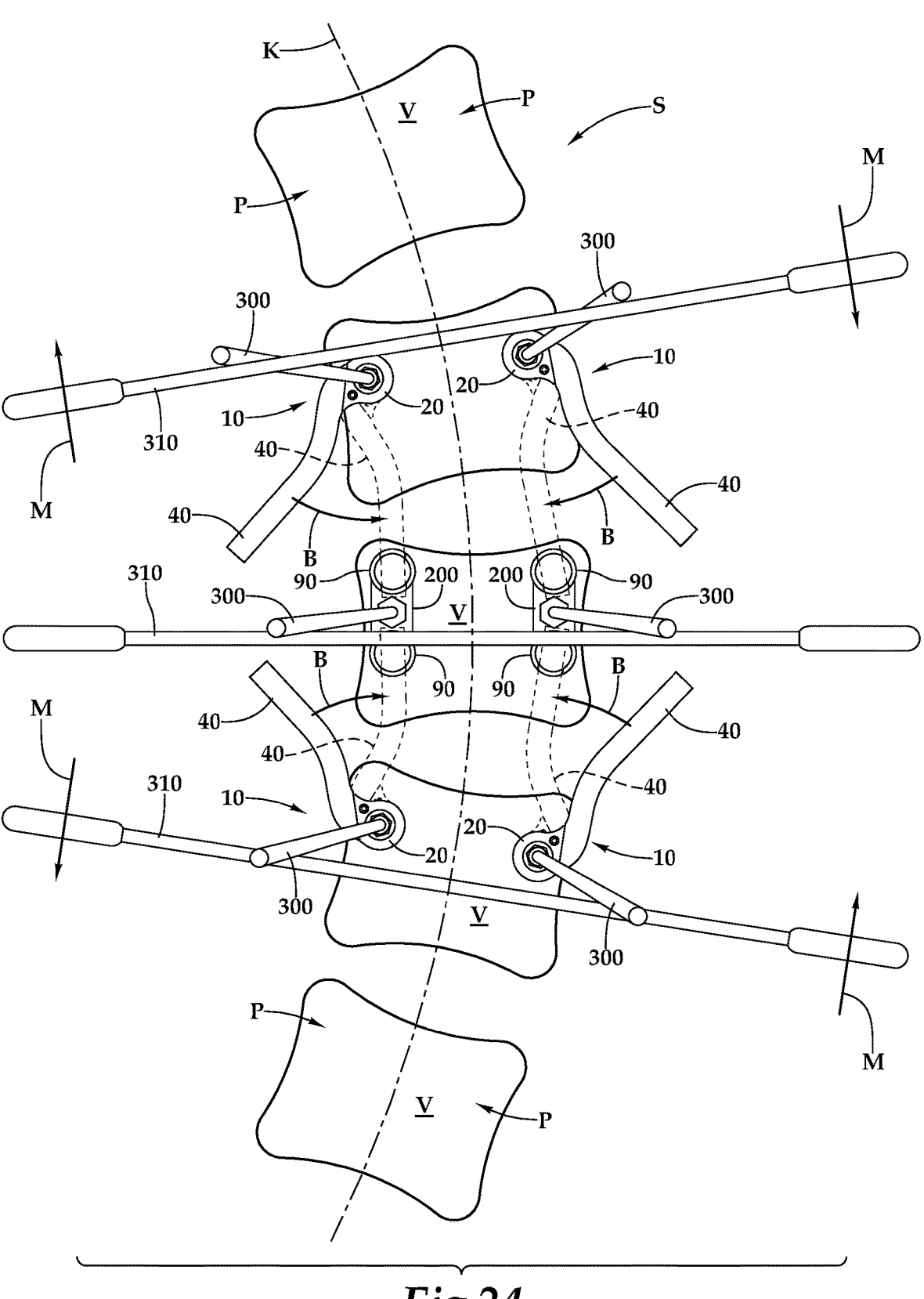
FIG. 24 is a plan view of a spine with scoliosis and with double tulip head assemblies and hybrid fixation assemblies of FIGS. 3-5 being used with other hardware to correct curvature.
Figure 25:
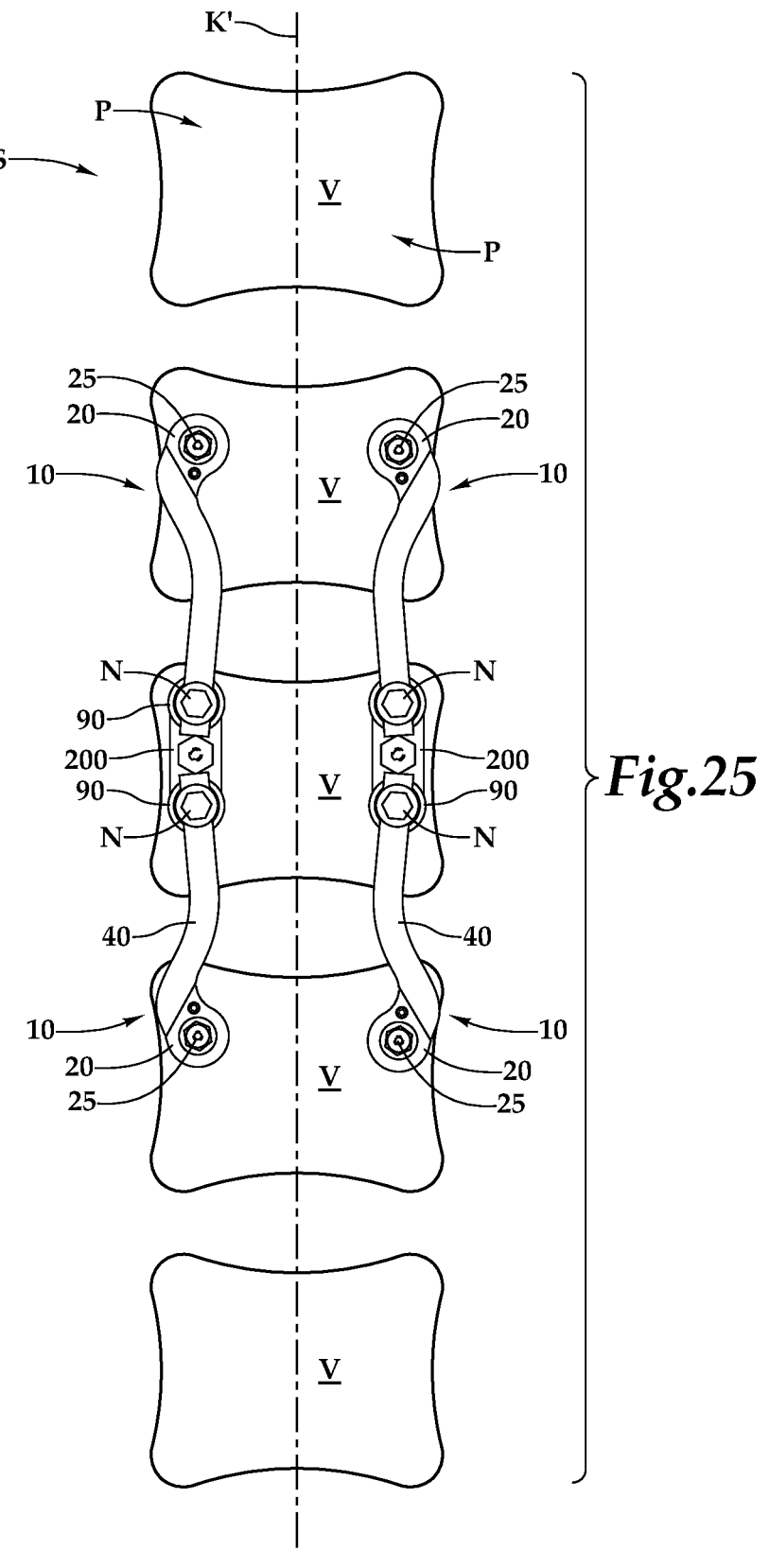
FIG. 25 is a plan view similar to FIG. 24 but after spine straightening.

One example of use of assemblies 10 along with the double tulip head assembly 200 is depicted in FIGS. 24 and 25 for correction of scoliosis. First an apex of the curvature K in the spine S is identified and an apex vertebra V is identified which is closest to a center of this curve. Pedicles P of this apex vertebra V each have a double tulip head assembly 200 affixed thereto and with a long axis of the bar 210 of each double tulip assembly 200 generally oriented parallel with a center line of the spine S (FIG. 24).

As a next step, a vertebra V adjacent to the apex vertebra has assemblies 10 affixed to pedicles P of these adjacent vertebra V. One assembly 10 goes into each pedicle P of each adjacent vertebra V. Assembly 10 has at least one degree of freedom and is loosened, such as by loosening the setscrew 50, so that the spine rod 40 can at least partially swivel (along arrow B) relative to the head 20 of the assembly 10.

Towers 300 are attached to the threaded bores 25 of each of the heads 20 of each of the assemblies 10. Furthermore, the threaded bore 225 at the central head 221 of the bar 210 of the double tulip assembly 200 also has a tower 300 attached thereto. Portions of the towers 300 which are attached to the apex vertebra V can have reduction rods 310 attached thereto, such as with the reduction rods 310 extending horizontally and near tips of the towers 300 most distant from the apex vertebra V. Similarly, towers 300 which are attached to the head 20 of the other assemblies 10 can have reduction rods 310 attached thereto which extend horizontally between the two towers associated with each vertebra V. Thus, one reduction rod 310 is associated with a single vertebrae and would typically have an orientation perpendicular to a central line of the spine S.

These reduction rods 310 can be manipulated, such as by surgeon, to cause them to be closer to parallel, reducing spine S to little or no curvature K'. If desired, further rods can be attached perpendicular to these horizontal reduction rods 310 to hold them in such a desirable parallel orientation, as the spine S is de-curved. Typically, some degree of surgical procedures are performed on the vertebra V and associated bodily structures, to more fully facilitate straightening of the spine S, to have a more linear form (when viewed from the rear). Once such a desired orientation for the spine S has been achieved, the spine rods 40 of each of the assemblies 10 can be pivoted down into the tulip heads 90 associated with the double tulip head assembly 200 (along arrow B of FIG. 24). Finally, nuts N can secure the spine rods 40 within these tulip heads 90 of the double tulip assembly 200 and various different set screws 50 and/or threaded pins 65, 79 can be tightened to complete the fixation procedure. The towers 300 and horizontal reduction rods 310 can then be removed and the spine S is left straightened as depicted in FIG. 25. Low profile hardware is all that remains securely holding the spine S so that it can maintain its de-curved form.

After the two vertebra V adjacent to the apex vertebra V have been fixed through the assemblies 10 and double tulip head assembly 200, further assemblies 10 can be affixed to pedicles P of vertebra V which are the next higher or the next lower vertebra V within the spine S. In such a way, further upper vertebrae and lower vertebrae can be included in the overall fixation system. Typically all vertebra V to be so fixed would have assemblies 10 attached thereto before straightening of the spine and removal of the towers 300 and reduction rods 310.

If, after a procedure is completed, it is desired to add further vertebra V into the overall fixation system, the threaded bore 25 in the head 20 of uppermost assemblies 10 and lowermost assemblies 10 is vacant and can have a turndown screw 80 and tulip head 90 attached thereto for conventional attachment of a spine rod R to another pedicle screw PS of an adjacent vertebra V (or spine rod 40 of an assembly 10). Alternatively, turndown screw 80 could be a portion of the first assembly 100 (FIG. 13) to provide a low profile further extension which could have its spine rod 140 attached to a standard pedicle screw PS with tulip heads T attached to a pedicle P of the next adjacent vertebra V.

As can readily be seen, utilizing different assemblies 10, 100, 200, and variations thereof, such as to include rotary joints 60 and donut collars 70, as well as turndown screws 80 and tulip heads 90, a large variety of different overall fixation systems can be contemplated and executed. Thus, assemblies of this invention provide the skilled surgeon with valuable tools to accommodate a wide variety of fixation needs, while maintaining flexibility to facilitate treatment of a wide variety of anatomical situations, and while also being low profile to minimize extension thereof in a posterior/dorsal direction.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A spine fixation assembly, comprising in combination:
a pedicle screw portion;
a spine rod portion;

said pedicle screw portion having an elongate threaded shaft extending along a rotational axis away from a head, said head having a torque receiving structure associated therewith;

said head including a truncated plane of swivel located lateral to said rotational axis of said pedicle screw portion, at least where said plane of swivel is adjacent to said head of said pedicle screw;

a junction on a proximal end of said spine rod portion, said junction having a face adjacent to said plane of swivel;

a swivel post extending perpendicular to said plane of swivel and joining said junction of said spine rod portion to said head of said pedicle screw portion, with rotation of said junction of said spine rod portion relative to said head of said pedicle screw portion about said swivel post;

a lock for selectively locking and unlocking said head of said pedicle screw portion to said junction of said spine rod portion against swivel of said spine rod portion relative to said pedicle screw portion;

wherein said lock includes a swivel set screw rotatable to selectively lock said head of said pedicle screw portion to said junction of said spine rod portion; and wherein said lock includes said swivel set screw having a conical tip which engages a beveled end of a sliding lock pin, said sliding lock pin oriented to engage said junction across said plane of swivel, and with said swivel set screw on a side of said plane of swivel opposite said junction.

2. The fixation assembly of claim 1 wherein a donut collar surrounds at least a portion of a central driving head portion of said head of said pedicle screw portion, said donut collar having said truncated plane of swivel thereon and said swivel post coupled thereto, said donut collar rotatable relative to said driving head of said pedicle screw portion, and with a threaded fastener selectively locking said donut collar to said driving head of said pedicle screw portion.

3. The fixation assembly of claim 2 wherein said lock includes a swivel set screw on said donut, said swivel set screw rotatable to selectively lock said donut collar of said pedicle screw portion to said junction of said spine rod portion.

4. The fixation assembly of claim 1 wherein said spine rod portion includes a rotary joint between said junction and a distal end opposite said junction, and wherein a spine rod fastener selectively locks said distal end of said spine rod portion to said junction of said spine rod portion.

5. The fixation assembly of claim 1 wherein a distal end of said spine rod is removably attachable to a tulip head, which tulip head is itself coupled to a pedicle of a vertebra separate from a vertebra that said threaded shaft of said pedicle screw portion is attached to.

6. The fixation assembly of claim 1 wherein said spine rod and said junction extend no further along said rotational axis of said pedicle screw than said driving head of said pedicle screw, such that a low profile is maintained.

7. The fixation assembly of claim 6 wherein a donut collar surrounds at least a portion of a central driving head of said head of said pedicle screw portion, said donut collar having said truncated plane of swivel thereon and said swivel post coupled thereto, said donut collar rotatable relative to said driving head of said pedicle screw portion, and with a threaded fastener selectively locking said donut collar to said driving head of said pedicle screw portion; and wherein said donut collar also extends no further along said rotation axis of said pedicle screw portion than said driving head of said pedicle screw portion.

8. The fixation assembly of claim 1 wherein a threaded bore is located extending down into said head along said rotational axis of said pedicle screw portion.

9. The fixation assembly of claim 8 wherein said threaded bore is located within said torque receiving structure.

10. A spine fixation assembly, comprising in combination:
a pedicle screw portion;
a spine rod portion;
said pedicle screw portion having an elongate threaded shaft extending along a rotational axis away from a head, said head having a torque receiving structure associated therewith;
said head including a truncated plane of swivel located lateral to said rotational axis of said pedicle screw portion, at least where said plane of swivel is adjacent to said head of said pedicle screw;
a junction on a proximal end of said spine rod portion, said junction having a face adjacent to said plane of swivel;
a swivel post extending perpendicular to said plane of swivel and joining said junction of said spine rod portion to said head of said pedicle screw portion, with rotation of said junction of said spine rod portion relative to said head of said pedicle screw portion about said swivel post;
a lock for selectively locking and unlocking said head of said pedicle screw portion to said junction of said spine rod portion against swivel of said spine rod portion relative to said pedicle screw portion;
wherein a donut collar surrounds at least a portion of a central driving head portion of said head of said pedicle screw portion, said donut collar having said truncated plane of swivel thereon and said swivel post coupled thereto, said donut collar rotatable relative to said driving head of said pedicle screw portion, and with a threaded fastener selectively locking said donut collar to said driving head of said pedicle screw portion;
wherein said lock includes a swivel set screw on said donut, said swivel set screw rotatable to selectively lock said donut collar of said pedicle screw portion to said junction of said spine rod portion; and
wherein said lock includes said swivel set screw having a conical tip which engages a beveled end of a sliding lock pin, said sliding lock pin oriented to engage said junction across said plane of swivel, and with said swivel set screw on a side of said plane of swivel opposite said junction.

11. A spine fixation assembly, comprising in combination:
a pedicle screw portion;
a spine rod portion;
said pedicle screw portion having an elongate threaded shaft extending along a rotational axis away from a head, said head having a torque receiving structure associated therewith;
said head including a truncated plane of swivel located lateral to said rotational axis of said pedicle screw portion, at least where said plane of swivel is adjacent to said head of said pedicle screw;
a junction on a proximal end of said spine rod portion, said junction having a face adjacent to said plane of swivel;
a swivel post extending perpendicular to said plane of swivel and joining said junction of said spine rod portion to said head of said pedicle screw portion, with rotation of said junction of said spine rod portion relative to said head of said pedicle screw portion about said swivel post;
a lock for selectively locking and unlocking said head of said pedicle screw portion to said junction of said spine rod portion against swivel of said spine rod portion relative to said pedicle screw portion;
wherein a threaded bore is located extending down into said head along said rotational axis of said pedicle screw portion;
wherein said threaded bore is located within said torque receiving structure; and
wherein said torque receiving structure is a recess extending into an upper surface of said head, said recess having faceted lateral sides with which a torque applying tool can engage, for rotation of said pedicle screw portion about said rotational axis and engagement of said threaded shaft of said pedicle screw portion with a pedicle of a vertebra.

12. A spine fixation assembly, comprising in combination:
a pedicle screw portion;
a spine rod portion;
said pedicle screw portion having an elongate threaded shaft extending along a rotational axis away from a head, said head having a torque receiving structure associated therewith;
said head including a truncated plane of swivel located lateral to said rotational axis of said pedicle screw portion, at least where said plane of swivel is adjacent to said head of said pedicle screw;
a junction on a proximal end of said spine rod portion, said junction having a face adjacent to said plane of swivel;
a swivel post extending perpendicular to said plane of swivel and joining said junction of said spine rod portion to said head of said pedicle screw portion, with rotation of said junction of said spine rod portion relative to said head of said pedicle screw portion about said swivel post;
a lock for selectively locking and unlocking said head of said pedicle screw portion to said junction of said spine rod portion against swivel of said spine rod portion relative to said pedicle screw portion;
wherein a threaded bore is located extending down into said head along said rotational axis of said pedicle screw portion; and
wherein a turndown screw having a body with a threaded shaft extending therefrom is threaded into said threaded bore of said head, with a tulip head at least partially interposed between said turn down screw and said head and with portions of said tulip head extending to a side of said turndown screw opposite said head, said tulip head configured to receive and hold a spine rod therein.

13. The fixation assembly of claim 12 wherein said spine rod is a spine rod portion of a separate fixation assembly including a pedicle screw portion, and with said spine rod portion and said pedicle screw portion attached together about a swivel post to cause swiveling within a swivel plane which is offset from a rotational axis of said pedicle screw portion.

14. A spine fixation assembly, comprising in combination:
a pedicle screw portion;
a spine rod portion;
said pedicle screw portion having an elongate threaded shaft extending along a rotational axis away from a head, said head having a torque receiving structure associated therewith;

said head including a truncated plane of swivel located lateral to said rotational axis of said pedicle screw portion, at least where said plane of swivel is adjacent to said head of said pedicle screw;

a junction on a proximal end of said spine rod portion, said junction having a face adjacent to said plane of swivel;

a swivel post extending perpendicular to said plane of swivel and joining said junction of said spine rod portion to said head of said pedicle screw portion, with rotation of said junction of said spine rod portion relative to said head of said pedicle screw portion about said swivel post;

a lock for selectively locking and unlocking said head of said pedicle screw portion to said junction of said spine rod portion against swivel of said spine rod portion relative to said pedicle screw portion; and wherein said spine rod includes a distal portion opposite said junction which is selectively capturable adjacent to a tulip head, said tulip head coupled to a double tulip head assembly including a bar with at least two lateral heads thereon and one central head, said central head including a torque receiving structure aligned with a rotational access thereof, and with a threaded shaft extending alongside said rotational axis on a side of said bar opposite said torque receiving structure, and with said lateral heads each including threaded bores extending into said bar on a side of said bar opposite said threaded shaft, each of said threaded bores having a turndown screw attached thereto, with a tulip head at least partially captured between said turndown screw and said bar of said double tulip head assembly, said spine rod captured to one of said tulip heads and with another of said tulip heads available to capture a separate spine rod.

15. The fixation assembly of claim 14 wherein said threaded shaft has threads configured to be placed within a pedicle of a vertebra.

16. The fixation assembly of claim 15 wherein a second said tulip head coupled to said bar having a spine rod captured thereto, which spine rod is a spine rod portion of a separate fixation assembly including a pedicle screw portion, and with said spine rod portion and said pedicle screw portion attached together about a swivel post to cause swiveling within a swivel plane which is offset from a rotational axis of said pedicle screw portion.

17. The fixation assembly of claim 16 wherein said central threaded bore extending from a side of said bar opposite said threaded shaft of said double tulip head assembly has a tower coupled thereto and wherein a tower is also coupled to a threaded bore located on a side of said head opposite said threaded shaft, said towers movable to cause relative repositioning of vertebrae to which the tulip head assembly and the pedicle screw portion are attached.

* * * * *